Figure 1A:
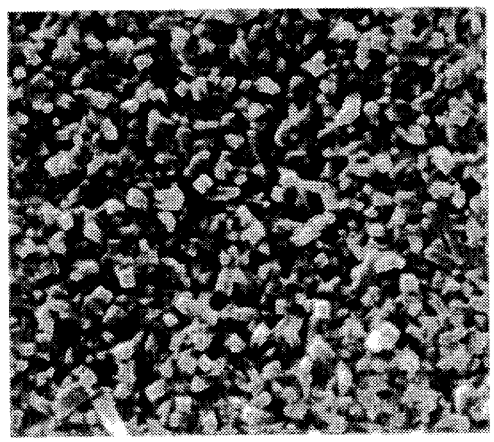

United States Patent [19]

Mueller et al.

[11] Patent Number: 5,525,323
[45] Date of Patent: Jun. 11, 1996

[54] PENTASIL ZEOLITES AGGLOMERATED IN THE FORM OF HOLLOW SPHERES

[75] Inventors: Ulrich Mueller, Neustadt; Axel Reich, Schornsheim; Klaus Unger, Seeheim-Jugenheim, all of Germany

[73] Assignee: BASF Aktiengesellschaft, Ludwigshafen, Germany

[21] Appl. No.: 266,353

[22] Filed: Jun. 30, 1994

[30] Foreign Application Priority Data

Jul. 15, 1993 [DE] Germany .................... 43 23 774.6

[51] Int. Cl.$^6$ .................................. C01B 39/36
[52] U.S. Cl. .................. 423/705; 423/708; 423/716; 423/DIG. 22; 423/DIG. 29; 423/DIG. 34
[58] Field of Search ................... 423/704, 705, 423/708, 716, DIG. 22, DIG. 29, DIG. 34; 502/77

[56] References Cited

U.S. PATENT DOCUMENTS

| | | | |
|---|---|---|---|
| 4,091,007 | 5/1978 | Dwyer et al. | 423/DIG. 22 |
| 4,108,881 | 8/1978 | Rollmann et al. | 423/708 |
| 4,139,600 | 2/1979 | Rollmann et al. | 423/708 |
| 4,205,053 | 5/1980 | Rollmann et al. | 423/DIG. 22 |
| 4,401,637 | 8/1983 | Marosi et al. | 423/705 |
| 4,456,582 | 6/1984 | Marosi et al. | 423/708 |
| 4,551,321 | 11/1985 | Marosi et al. | 423/708 |
| 4,818,509 | 4/1989 | Dwyer et al. | 502/77 |
| 4,891,451 | 1/1990 | Hoelderich et al. | 568/691 |
| 4,960,894 | 10/1990 | Hoelderich et al. | 546/250 |
| 5,225,602 | 7/1993 | Hoelderich et al. | 568/41 |
| 5,240,892 | 8/1993 | Klocke | 502/77 |

FOREIGN PATENT DOCUMENTS

| | | | |
|---|---|---|---|
| 65401 | 11/1982 | European Pat. Off. . | |
| 72054 | 2/1983 | European Pat. Off. . | |
| 0093519 | 11/1983 | European Pat. Off. | 423/716 |
| 219804 | 4/1987 | European Pat. Off. . | |
| 3546372 | 7/1987 | Germany . | |
| 3634247 | 7/1987 | Germany . | |
| 1124524 | 8/1968 | United Kingdom | 423/716 |

*Primary Examiner*—Mark L. Bell
*Assistant Examiner*—David R. Sample
*Attorney, Agent, or Firm*—John H. Shurtleff

[57] ABSTRACT

Abstract of the Disclosure: Pentasil zeolites agglomerated in the form of hollow spheres and having a particle size of from 5 to 200 micron are prepared by treating a mixture of an aqueous alkylenediamine, alkylenetriamine and/or alkylenetetramine, silica and an aluminum, boron and/or titanium salt at from 20° to 100° C., then crystallizing the product at from 110° to 200° C. and from 0.01 to 50 bar and calcining it at from 400° to 650° C., and said zeolites are used as catalysts and/or adsorbents.

16 Claims, 1 Drawing Sheet

10 μm

1 μm

10 μm

PENTASIL ZEOLITES AGGLOMERATED IN THE FORM OF HOLLOW SPHERES

The present invention relates to pentasil zeolites agglomerated in the form of hollow spheres and having a particle size of from 5 to 200 micron, whose preparation is effected by treating a mixture of an aqueous alkylenediamine, alkylenetriamine and/or alkylenetetramine, silica and an aluminum, boron and/or titanium salt at from 20° to 100° C., and their use as catalysts or adsorbents.

Zeolites are known to be crystalline aluminosilicates which have ordered channel and cage structures and whose pore openings are in the range of micropores of less than 0.9 nm. The network of such zeolites is composed of $SiO_4$ and $AlO_4$ tetrahedra which are linked via common oxygen bridges. For example, W. M. Meier and D. H. Olson, Atlas of Zeolite Structure Types, 2nd Edition, Butterworths, London 1987, give an overview of the known structures.

Zeolites contain exchangeable cations to compensate the negative electrovalency resulting from the incorporation of Al(III) into the Si(IV) silicate lattice. If these cations are replaced with protons, for example by ion exchange, the correspondingly acidic solids having a zeolite structure, is the H form, are obtained. The most common synthesizable types, such as zeolite A, X and Y, are used industrially as molecular sieves, ion exchangers and catalysts. Silicon-rich pentasil zeolites are of particular interest for use as catalysts, owing to their thermal stability and their acidity. In these materials, the aluminum incorporated in the crystal lattice can be replaced by iron, gallium or boron while retaining the structure type, with the result that pentasil zeolites having a graded acidity are obtained (Post, Huizinga, Emeis, Nanne and Stork in Zeolites as Catalysts, Sorbents and Detergent Builders, and Karge, Weitkamp (Eds.), Elsevier (Amsterdam) 1989, pages 365 to 375).

Such acidic pentasil zeolites can be used for reactions of organic molecules under heterogeneous catalysis. In the preparation of organic intermediates, pentasil zeolites are used in the preparation of 3-acylpyridine from acrolein, ketones in acetal form and ammonia (EP-A-318 845), in the synthesis of amines from olefins and ammonia (DE-A-36 34 247), in the isomerization of epoxides (DE-A-35 46 372), and in the vinyl ether synthesis from acetals (DE-A-37 22 891) to mention but a few examples.

In the preparation of pentasil zeolites, the prior art reveals the possibilities of reacting aqueous alkaline mixtures comprising a silica source, a metal oxide source, sodium oxide and an organic template compound, for example tetra-n-propylammonium salts, hydrothermally under autogenous pressure. Such processes are described in, for example, EP-A-68 796. The use of piperidine or hexamethyleneimine as the organic template compound is disclosed in EP-A-293 032, and DE-A-28 30 787 and EP-A-7 081 show that metal silicate zeolites are also obtained in an alkali-free synthesis mixture with hexamethylenediamine.

Zeolites in the form of finely divided powders having particle sizes of from 0.5 to 3 micron are obtained from industrial crystallizations. In particular, the isolation (centrifuging filtration, washing), the handling and the processing of such materials to give catalysts or adsorbents increasingly present problems with regard to work safety (fine dust) and are time-consuming and therefore expensive.

It is an object of the present invention to remedy the abovementioned disadvantages and to provide pentasil zeolites in a form which can easily be handled.

We have found that this object is achieved by novel pentasil zeolites agglomerated in the form of hollow spheres and having a particle size of from 5 to 200 micron and a process for the preparation of said pentasil zeolites, wherein a mixture of an aqueous alkylenediamine, alkylenetriamine and/or alkylenetetramine, silica and an aluminum, boron and/or titanium salt is treated at from 20° to 100° C. and the product is then crystallized at from 110° to 200° C. and from 0.01 to 50 bar and calcined at from 400° to 650° C., and their use as catalysts and/or adsorbents.

The novel pentasil zeolites agglomerated in the form of hollow spheres can be prepared as follows: An aqueous alkylenediamine, alkylenetriamine and/or alkylenetetramine solution in the form of a 20–75, preferably 35–60, particularly preferably 50, % strength by weight solution, can be initially taken, for example in a pressure-resistant container, and the $SiO_2$ source, for example silica, silica gel, pyrogenic silica, particularly preferably silica prepared by a pyrogenic method, can be introduced while stirring, for example at from 10° to 40° C., as a rule at room temperature (from 18° to 25° C.). Examples of suitable stirrers are anchor stirrers. The stirring speed is as a rule from 20 to 500 rpm, preferably from 40 to 300, particularly preferably from 50 to 150, rpm.

In a separate mixing vessel, the aluminum, boron and/or titanium salt, preferably aluminum and/or boron salt, particularly preferably aluminum salt, such as halide, precipitated hydroxide, nitrate or sulfate, can be dissolved in demineralized water until a clear liquid is obtained. It has proven advantageous to use aluminum in the form of acidic salts, for example as the sulfate or nitrate. Boron is preferably used as boric acid and titanium preferably as titanyl sulfate.

This aluminum, boron and/or titanium solution can be preferably added very rapidly, for example by running in or rapid dropwise addition, to the suspension of aqueous alkylenediamine, alkylenetriamine and/or alkylenetetramine and $SiO_2$ source in the stirred pressure-resistant container, said suspension being kept at from 20° to 100° C., preferably from 40° to 80° C., particularly preferably from 60° to 75° C. For more thorough mixing, the stirring speed can be increased. As a rule, a gel is obtained and, for homogenization, is kept for several hours, as a rule from 0.2 to 100, preferably from 0.5 to 20, particularly preferably from 1 to 6, hours at the abovementioned temperatures and is then heated to the reaction temperature of from 110° to 200° C., preferably from 130° to 180° C., particularly preferably from 140° to 160° C., which is required for the crystallization. The pressure during the crystallization is, as a rule, from 0.01 to 50, preferably from 0.1 to 5, bar, autogenous pressure particularly preferably being used. The pentasil zeolites are generally formed in the course of from 1 to 8 days.

To isolate the product, the solid can be separated off from the cooled reacted mixture by filtration and the filter cake washed repeatedly with water. The novel process gives the pentasil zeolites in the form of relatively large agglomerates in the form of hollow spheres and having a particle size (diameter) of from 5 to 200, preferably from 10 to 100, micron, so that, in contrast to the zeolite powders which can be prepared according to the prior art, very short filtration and washing times of the agglomerates can be realized. Furthermore, the loss of zeolite product frequently associated with this operation and due to bleeding is substantially reduced.

The solid can then be dried at 120° C. The amine form of the pentasil zeolites agglomerated in the form of hollow spheres can be converted into the catalytically active H form of the zeolite by a heat treatment at from 400° to 650° C., preferably from 450° to 550° C., particularly preferably from 480° to 530° C.

The novel pentasil zeolites agglomerated in the form of hollow spheres have, as a rule, low bulk densities of from 150 to 280, preferably from 150 to 200, kg/m³ and improved flowability and fluidizability.

The novel materials can preferably be used as catalysts or adsorbents, for example in agitated beds, fluidized beds and suspensions.

In order to achieve a very high selectivity, a high conversion and long catalyst lives, it is advantageous to modify the novel zeolites. A suitable modification comprises doping the unmolded or molded material with metal salts by ion exchange or by impregnation. The metals used are alkali metals, such as Li, Cs or K, alkaline earth metals, such as Mg, Ca or Sr, metals of the 3rd, 4th and 5th main groups, such as Al, Ga, Ge, Sn, Pb or Bi, transition metals of the 4th to 8th subgroups, such as Ti, Zr, V, Nb, Cr, Mo, W, Mn, Re, Fe, Ru, Os, Co, Rh, Sr, Ni, Pd or Pt, transition metals of the 1st and 2nd subgroups, such as Cu, Ag or Zn, and rare earth metals, such as La, Cs, Pr, Nd, Fr, Yb and U.

The doping is advantageously carried out by a method in which the novel zeolites are initially taken in a riser tube and an aqueous or ammoniacal solution of a halide or of a nitrate of the metals described above is passed over at from 20° to 100° C. Ion exchange of this type can be carried out over the hydrogen, ammonium and alkali metal form of the material. A further possible method for applying metals to the hollow spheres is to impregnate the novel material, for example with a halide, a nitrate or an oxide of the metals described above, in aqueous, alcoholic or ammoniacal solution. Both ion exchange and impregnation are followed by at least one drying step or alternatively repeated calcination.

A possible embodiment comprises, for example, dissolving $Cu(NO_3)_2 \cdot 3H_2O$ or $Ni(NO_3)_2 \cdot 6H_2O$ or $Ce(No_3)_3 \cdot 6H_2O$ or $La(NO_3)_2 \cdot 6H_2O$ or $Cs_2CO_3$ in water. This solution is used to impregnate the agglomerated zeolite for a certain time (about 30 minutes). Any supernatant solution is freed from water in a rotary evaporator. Thereafter, the impregnated solid is dried at about 150° C. and calcined at about 550° C. This impregnation process can be carried out several times in succession in order to obtain the desired metal content.

It is possible to prepare an aqueous $Ni(CO_3)_2$ solution or ammoniacal $Pd(NO_3)_2$ solution and to suspend the hollow spherical agglomerates therein at from 40° to 100° C. in the course of about 24 hours while stirring. After filtration, drying at about 150° C. and calcination at about 500° C., the material thus obtained can, if required, then be further processed, with or without a binder, to give extrudates, pellets or fluidizable material. If this downstream molding process is carried out carefully, the hollow spherical structure can be used in this way in order to impart to the molded material a corresponding porosity in the range of large transport pores (1–50 micron).

The hollow spherical pentasil zeolite present in the H form or ammonium form or alkali metal form can be subjected to ion exchange by a method in which the material is initially taken in a column and, for example, an aqueous $Ni(NO_3)_2$ solution or ammoniacal $Pd(NO_3)_2$ solution is circulated over it at slightly elevated temperatures of from 30° to 80° C. for from 15 to 20 hours. Thereafter, the product is thoroughly washed with water, dried at about 150° C. and calcined at about 550° C. In the case of some metal-doped novel catalysts, for example doped with Pd, Cu or Ni, an aftertreatment with hydrogen is advantageous.

A further possible method of modification comprises subjecting the novel material, in molded or unmolded form, to a treatment with acids, such as hydrochloric acid, hydrofluoric acid and phosphoric acid, and/or steam. Advantageously, the zeolite in powder form is treated with 1N phosphoric acid for i hour at 80° C. After the treatment, the product is washed with water, dried at 110° C. for 16 hours and calcined at 500° C. for 20 hours.

In another procedure, the hollow spheres are treated, before or after they have been molded with binders, with a 3–25, in particular 12–20, % strength by weight aqueous hydrochloric acid for from 1 to 3 hours at from 60° to 80° C. The zeolite treated in this manner is then washed with water, dried, and calcined at from 400° to 500° C.

A particular embodiment for the acid treatment comprises treating the novel material, before it has been molded, at elevated temperatures with 0.001–2N, preferably 0.05–0.5N, hydrofluoric acid, for example by refluxing for from 0.5 to 5, preferably from 1 to 3, hours. After the novel material has been isolated by filtration and thorough washing, it is advantageously dried at from 100° to 160° C. and calcined at from 450° to 600° C. In a further preferred embodiment of the acid treatment, the novel material is molded with a binder and then treated with 12–20% strength by weight hydrochloric acid at elevated temperatures, advantageously at from 50° to 90° C., preferably from 60° to 80° C., for from 0.5 to 5 hours. The novel material is then washed thoroughly and advantageously dried at from 100° to 160° C. and calcined at from 450° to 600° C. An HF treatment may also be followed by an HCl treatment.

The modifications carried out on these catalysts can be effected in the gas phase at from 100° to 450° C., preferably from 150° to 350° C., particularly preferably from 200° to 300° C., and at a WHSV of from 0.1 to 20 $h^{-1}$, preferably from 0.5 to 5 $h^{-1}$ (g of starting mixture per g of catalyst per hour), in a fixed bed or, preferably, in a fluidized bed.

It is preferable to carry out the reaction in the liquid phase (suspension, trickle-bed or liquid phase procedure) at from 0° to 250° C., preferably from 50° to 150° C.

These processes are as a rule carried out at from 0.01 to 50, preferably from 0.1 to 5, bar, particularly preferably at atmospheric pressure or, depending on the volatility of the starting compound, at reduced or superatmospheric pressure, preferably continuously but also batchwise.

Poorly volatile or solid starting materials are used in dissolved form, for example in solution in tetrahydrofuran, toluene or petroleum ether. In general, dilution of the starting material in such solvents or with inert gases, such as $N_2$, Ar or steam, is possible.

After the reaction, the resulting products can be isolated from the reaction mixture by conventional methods, for example by distillations unconverted starting materials are, if required, recycled to the reaction. Owing to the novel agglomerated form of the zeolite, it is also possible to recover the catalyst from the reaction mixture by simple filtration.

Preferably, gaseous reaction products can be immediately introduced into a separation stage and separated into their individual components, for example in a fractionating column, in order to suppress a backreaction and to achieve a high conversion.

The novel pentasil zeolites agglomerated in the form of hollow spheres can be used as heterogeneous catalysts for nucleophilic and electrophilic substitutions, for addition and elimination reactions, for double bond and skeletal isomerizations, including rearrangement reactions, and, for example, for alkylations, isomerizations, disproportionations, acylations, cyclizations, hydrations, dehydrations, aminations, hydrogenations, dehydrogenations, dehydrocyclizations, hydroxylations and combinations of these reactions, for the controlled reaction of organic molecules. Reactions of this type are described in, for example, H ölderich, Zeolites: Catalysis for the synthesis of organic compounds, Stud. Surf. Sci. Catal. 49 (1989), 69–93, or H olderich and van Bekkum, Zeolites in organic syntheses, Elsevier, Stud. Surf. Sci. Catal. 58 (1991), 631–727. Dehydration reactions can be particularly advantageously carried out with the novel heterogeneous catalysts.

Examples are: Esterifications of carboxylic acids and alcohols, for example phthalic anhydride and higher alcohols in the liquid phase Etherifications of alcohols Cyclizations of diols, e.g. 1,4-butanediol to give tetrahydrofuran.

Furthermore, both double bond isomerizations and skeletal isomerizations can be carried out using the novel pentasil zeolites as heterogeneous catalysts.

These include: Epoxide rearrangement, ie. conversion of an epoxide into an aldehyde or ketone, e.g. styrene oxide and its derivatives into the corresponding phenylacetaldehydes. Beckmann rearrangement, for example of cyclohexanone oxime into $\epsilon$-caprolactam.

Furthermore, both the acid-catalyzed and, in the case of correspondingly modified catalysts, the base-catalyzed aldol condensation can be carried out with the novel catalysts. Examples are: Acetone to mesityl oxide Butyraldehyde to 2-ethylhexanal Acrolein, formaldehyde and $NH_3$ to pyridine and $\beta$-picoline.

The novel zeolites can also be used as carriers for catalytically active components, such as metals, by application via impregnation or ion exchange, as mentioned above, for example for noble metals in hydrogenation and oxidation reactions.

In addition to the catalytic properties, the agglomerates also have adsorption and ion exchange capacity and the novel materials can also be used as adsorbents for organic and inorganic compounds.

EXAMPLES

EXAMPLE 1

This Comparative Example describes the crystallization of pentasil zeolites without the agglomeration according to the invention. 14.2 kg of an aqueous hexamethylenediamine solution (50% by weight in demineralized water) and 13.5 kg of demineralized water were initially taken in a stirred pressure-resistant container. 4.6 kg of silica (Aerosil®200 from Degussa) were added to this mixture while stirring, and the batch was homogenized at a stirring speed of 150 rpm. A clear solution was prepared from 1.01 kg of aluminum sulfate 18-hydrate (Merck) and 6.76 kg of water, and was added to the reaction batch. The resulting viscous reaction gel was homogenized at 100 rpm and heated to 150° C. The crystallization was carried out at 150° C. for 168 hours. The cooled reaction mixture was discharged from the reactor, and the pentasil zeolite formed was separated off from the mother liquor.

Filtration of the mother liquor and washing neutral on a pressure filter (3 bar, 250 l nominal capacity) lasted 2–3 hours. The initially bleeding filtrate had to be circulated several times over the filter cake to avoid further product loss. The yield of zeolite was 74%, based on silica used. The bulk density of the dried reaction product calcined at 500° C. for 12 hours was 407 $kg/m^3$. The size of the primary crystallites was from 0.2 to 1 micron, determined from scanning electron micrographs; X-ray analysis showed that the crystalline product was the aluminosilicate zeolite described in EP-A-7 081.

EXAMPLE 2

14.2 kg of an aqueous hexamethylenediamine solution (50% by weight in demineralized water) and 13.4 kg of demineralized water were initially taken in a stirred pressure-resistant container. 4.6 kg of silica (Aerosil®200 from Degussa) were added to this stirred mixture in the course of 15 minutes, and the batch was homogenized at a stirring speed of 150 rpm.

A clear solution was prepared from 1.01 kg of aluminum sulfate 18-hydrate (Merck) and 6.76 kg of water. In contrast to Example 1, the reaction batch was initially heated to 70° C. and the aluminum sulfate solution was then added rapidly at a stirrer speed of 250 rpm. The reaction gel formed was homogenized at 100 rpm for a further four hours before being heated to 150° C. The crystallization was carried out at 150° C. for 168 hours. The cooled reaction mixture was discharged from the reactor, and the pentasil zeolite formed was separated off from the mother liquor. The filtration of the mother liquor required only about 20 minutes. No bleeding of the filtrate was found. The yield of zeolite was quantitative, based on silica used. The bulk density of the dried reaction product calcined at 500° C. for 12 hours was 173 $kg/m^3$. X-ray analysis showed that the crystalline product was the aluminosilicate zeolite described in EP-A-7 081.

Figure 1B:
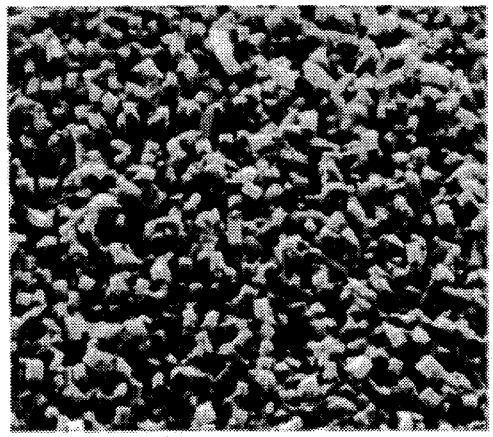
Figure 2A:
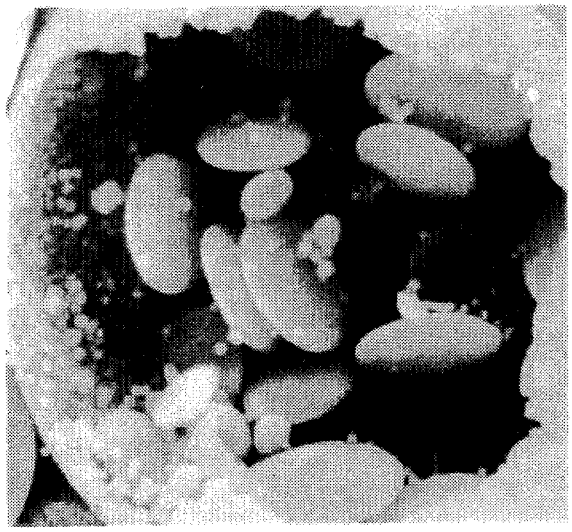
Figure 2B:
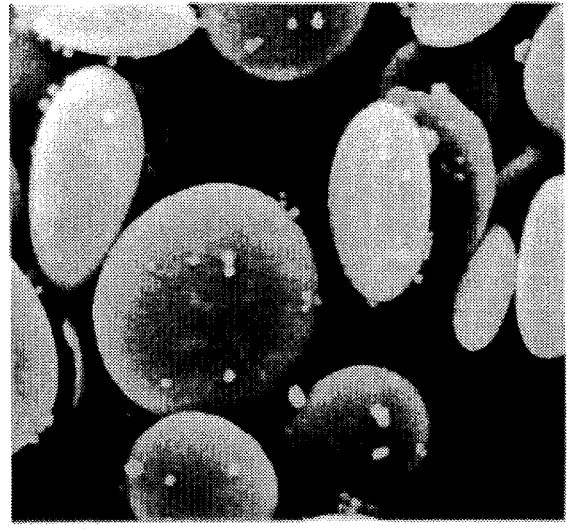

The following scanning electron micrograph in FIGS. 1a and 1b show that the product comprises intergrown primary crystallites having a size of from about 0.1 to 0.2 micron. FIGS. 2a and 2b shows that these intergrowths occur in a regular manner in the form of egg-shaped hollow spheres, the size of the hollow spheres being from about 10 to 100 micron. The shell thickness of such hollow spheres is often only from 2 to 5 micron.

We claim:

1. A pentasil zeolite of intergrown primary crystallites agglomerated in the form of egg-shaped hollow spheres which have a size of about 5 to 200 micron.

2. A pentasil zeolite as claimed in claim 1, wherein the size of the spheres is about 10 to 100 micron.

3. A pentasil zeolite as claimed in claim 1, wherein the spheres provide a bulk density for the zeolite of from 150 to 280 $kg/m^3$.

4. A pentasil zeolite as claimed in claim 1, wherein the spheres provide a bulk density for the zeolite of from 150 to 200 $kg/m^3$.

5. A pentasil zeolite as claimed in claim 1, wherein the shell thickness of the hollow spheres is about 2 to 5 microns.

6. A pentasil zeolite as claimed in claim 1, wherein the spheres have a size of about 10 to 100 micron and a shell thickness of about 2 to 5 microns to provide a bulk density for the zeolite of from 150 to 200 $kg/m^3$, and the primary crystallites which are agglomerated to form said spheres have a particle size of from about 0.1 to 0.2 micron.

7. A process for the preparation of a pentasil zeolite in which intergrown primary crystallites are agglomerated in the form of egg-shaped hollow spheres, which comprises:

stirring a liquid mixture of $SiO_2$ and an aqueous solution of at least one amine selected from the group consisting of alkylenediamines, alkylenetriamines and alkylenetetramines and admixing therewith an aqueous solution of at least one cation selected from the group consisting of aluminum, boron and titanium at a temperature of from 10° to 100° C. and for a period of time sufficient to obtain an homogeneous slurry comprising agglomerated but still amorphous gel particles having a size of about 5 to 200 microns;

then heating the resulting mixture for crystallization of said particles at a temperature of from 110° to 200° C. and a pressure of from 0.01 to 50 bar; and thereafter cooling and separating the solid crystallized product.

8. A process as claimed in claim 7, wherein the agglomerated and crystallized product is calcined at a temperature of from 400° to 650° C.

9. The product obtained by the process of claim 8.

10. A process as claimed in claim 7, wherein the $SiO_2$ and amine components are initially stirred at a temperature of from 10° to 40° C. and a stirring speed of from 20 to 500 rpm, and the exchangeable cation is subsequently admixed with said stirring continued at a temperature of from 20° to 100° C.

11. A process as claimed in claim 7, wherein the exchangeable cation is provided by the addition of boric acid or a salt of aluminum, titanium or boron, and the liquid mixture is essentially free of alkali or alkaline earth metal compounds.

12. A process as claimed in claim 7, wherein the amine is added as an aqueous 20–75% strength solution.

13. A process as claimed in claim 7, wherein the amine is selected from the group consisting of diethylenetriamine, triethylenetetramine, propylenediamine, dipropylenetriamine, hexamethylenediamine and dihexamethylenetriamine.

14. A process as claimed in claim 8, wherein the pentasil zeolite is modified by doping the solid crystallized and agglomerated product, before or after calcination, with a salt of a metal selected from the group consisting of alkali metals, alkaline earth metals, metals of the 3rd, 4th and 5th main group, transition metals of the 4th to 8th subgroups, transition metals of the 1st and 2nd subgroups and rare earth metals, all with reference to the Periodic Table of Elements.

15. A process as claimed in claim 8, wherein the pentasil zeolite is modified after calcination, by treatment with an acid, by treatment with a steam or by treatment with both acid and steam.

16. A process as claimed in claim 8, wherein the calcined product is subsequently molded, optionally with a binder, to provide larger shaped structures in the form of extrudates, pellets or a fluidizable material.

\* \* \* \* \*